United States Patent [19]

Murakami

[11] Patent Number: 5,238,828
[45] Date of Patent: Aug. 24, 1993

[54] METHOD FOR THE PREPARATION OF AN OPTICALLY ACTIVE 2-SUBSTITUTED CARBOXYLIC ACID

[75] Inventor: Nobuo Murakami, Sodegaura, Japan

[73] Assignee: Idemitsu Kosan Company Limited, Tokyo, Japan

[21] Appl. No.: 760,824

[22] Filed: Sep. 17, 1991

Related U.S. Application Data

[63] Continuation of Ser. No. 393,591, Aug. 14, 1989, abandoned.

[30] Foreign Application Priority Data

Aug. 29, 1988 [JP] Japan ................... 63-212536
Dec. 19, 1988 [JP] Japan ................... 63-318587
May 30, 1989 [JP] Japan ................... 1-134743

[51] Int. Cl.$^5$ .................. C12P 7/40; C12P 17/02; C12P 7/64; C12N 9/78
[52] U.S. Cl. .................. 435/136; 435/227; 435/280; 435/123
[58] Field of Search ............ 435/136, 227, 929, 874, 435/280, 123

[56] References Cited

U.S. PATENT DOCUMENTS

| | | | |
|---|---|---|---|
| 4,001,081 | 1/1977 | Commeyras et al. | 435/832 |
| 4,080,259 | 3/1978 | Boester et al. | 435/228 |
| 4,443,548 | 4/1984 | Oshima et al. | 435/280 |
| 4,637,982 | 1/1987 | Yamada et al. | 435/228 |

FOREIGN PATENT DOCUMENTS

| | | |
|---|---|---|
| 0193113 | 9/1986 | European Pat. Off. . |
| 0326482 | 8/1989 | European Pat. Off. . |
| 0330529 | 8/1989 | European Pat. Off. . |
| 0348901 | 1/1990 | European Pat. Off. . |
| WO86/07386 | 12/1986 | World Int. Prop. O. . |

OTHER PUBLICATIONS

Goodfellow et al. "Biology of the Actiuowycetes", Academiclress, 1984, pp. 44-46.

*Primary Examiner*—Irene Marx
*Attorney, Agent, or Firm*—Frishauf, Holtz, Goodman & Woodward

[57] ABSTRACT

An efficient microbiological or biochemical method is proposed for the preparation of an optically active 2-substituted carboxylic acid, e.g., 2-chloropropionic acid, 2-methyl butyric acid and the like, from the corresponding 2-substituted nitrile compound, e.g., 2-chloropropionitrile, 2-methyl butyronitrile and the like, in the form of a racemic body as the starting material The method comprises bringing the starting nitrile compound into contact with a microorganism, such as Pseudomonas sp. MY-1 (FERM BP-2541), Fusarium sp. MY-2 (FERM BP-2542) and the like, capable of converting the nitrile compound into the carboxylic acid in a buffered aqueous medium in which the microbial cells of the microorganism are suspended.

8 Claims, No Drawings

METHOD FOR THE PREPARATION OF AN OPTICALLY ACTIVE 2-SUBSTITUTED CARBOXYLIC ACID

This application is a continuation of application Ser. No. 07/393,591, filed Aug. 14, 1989, now abandoned.

BACKGROUND OF THE INVENTION

The present invention relates to a method for the preparation of an optically active 2-substituted carboxylic acid. More particularly, the invention relates to a method for the preparation of an optically active 2-substituted carboxylic acid useful as an intermediate for the synthesis of various kinds of medicinal and agricultural chemicals and as a starting material of liquid-crystalline polymers Several synthetic methods are known for the preparation of an optically active 2-substituted carboxylic acid but none of the known methods is fully efficient from the standpoint of industrial production. It is expected that there can be a microbiological method for the preparation of an optically active 2-substituted carboxylic acid in a much higher efficiency than in any of the known chemical synthetic methods but no such a microbiological method is known in the prior art.

SUMMARY OF THE INVENTION

The present invention accordingly has an object to provide a novel and very efficient microbiological method for the preparation of an optically active 2-substituted carboxylic acid.

Thus, the present invention provides a microbiological method for the preparation of an optically active 2-substituted carboxylic acid represented by the general formula

(I)

in which: (A) R is a group selected from the class consisting of alkyl groups unsubstituted or substituted with a hydroxy group, sulfuhydryl group, amino group or halogen atom, alkenyl groups, and phenyl and naphthyl groups unsubstituted or substituted with a hydroxy group, alkyl group having 1 to 5 carbon atoms, alkoxy group having 1 to 5 carbon atoms or halogen atom, and X is a methyl group, ethyl group or halogen atom with the proviso that R and X are not simultaneously a methyl group or an ethyl group; or (B) R is a divalent group of the formula

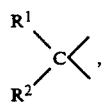

where $R^1$ and $R^2$ each being a hydrogen atom or a lower alkyl group, and X is a divalent group of the formula

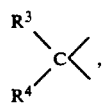

wherein $R^3$ being a hydrogen atom or a lower alkyl group and $R^4$ being a hydrogen atom, lower alkyl group or a group of the formula $Z_2C=CH-$ where Z is a halogen atom or a lower alkyl group, with the proviso that R and X jointly form a cyclopropane ring together with the carbon atom to which each of R and X is bonded and that all of $R^1$ and $R^2$ in R and $R^3$ and $R^4$ in X are not of the same kind of atoms or groups, which comprises bringing a racemic 2-substituted nitrile compound represented by the general formula

(II)

in which R and X each have the same meaning as defined above, into contact with a microorganism capable of converting the racemic 2-substituted nitrile compound into the optically active 2-substituted carboxylic acid of the general formula (I).

Alternatively, the inventive method for the preparation of the optically active 2-substituted carboxylic acid represented by the above given general formula (I) comprises bringing a racemic body of the 2-substituted nitrile compound represented by the above given general formula (II) into contact with a first enzyme capable of converting the racemic 2-substituted nitrile compound into a carboxylic acid amide represented by the general formula

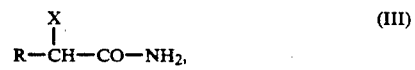
(III)

in which R and X each have the same meaning as defined above, and a second enzyme capable of converting the carboxylic acid amide represented by the above given general formula (III) into the optically active 2-substituted carboxylic acid represented by the above given general formula (I).

Further alternatively, the inventive method for the preparation of the optically active 2-substituted carboxylic acid represented by the above given general formula (I) comprises bringing a racemic 2-substituted nitrile compound represented by the above given general formula (II) into contact with an enzyme capable of converting the racemic 2-substituted nitrile compound into the optically active 2-substituted carboxylic acid.

DETAILED DESCRIPTION OF THE PREFERRED EMBODIMENTS

The starting material used in the above described inventive method is a racemic 2-substituted nitrile compound represented by the above given general formula (II) in which the symbols R and X each have the meaning as defined. Particular examples of the 2-substituted nitrile compound to which the inventive method is applicable include 2-methylbutyronitrile, 2-methylvaleronitrile, 2-methylhexylonitrile, -methyl-3-hydroxypropionitrile, 2-methyl-3-sulfuhydroxypropionitrile, 2-methyl-3-chloropropionitrile, 2-methyl-3-aminopropionitrile, 2-chloropropionitrile, 2,3-dichloropropionitrile, 2-chlorobutyronitrile, 2,3-dichlorobutyronitrile, 2-phenylpropionitrile, 2-(4-isobutylphenyl)propionitrile, 2-methyl-3-butenonitrile, 1-cyano-2,2-dimethylcyclopropane and the like.

In an embodiment of the invention, the above described racemic 2-substituted nitrile compound is brought into contact with a microorganism capable of converting the nitrile compound into the desired optically active 2-substituted carboxylic acid. The microorganism suitable for the purpose belongs to one of the genera of Pseudomonas, Fusarium, Rhodococcus, Brevibacterium, Micrococcus, Bacteridium and Bacillus, but the species thereof is not particularly limitative provided that the microorganism has an activity to convert the racemic body of the 2-substituted nitrile compound into the optically active 2-substituted carboxylic acid. Particular examples of the preferable microorganism include Pseudomonas sp. MY-1 (FERM P-9174, FERM BP-2541 ), Fusarium sp. MY-2 (FERM P-9187, FERM BP-2542 ), *Rhodococcus erythropolys* (IFO 12320), *Brevibacterium imperial* B222 (CBS 498.74), Micrococcus sp. A1ll (CBS 497.74), Bacteridium sp. R341 (CBS 496.74), Bacillus sp. (CBS 494.74) and the like. (The depository and address therefore for FERM deposits is:

Fermentation Research Institute, Agency of Industrial Science and Technology, Ministry of International Trade and Industry, 1-3, Higashi 1-chrome, Tskukubashi, Ibaraki-ken, Japan;

and the depository and address therefore for IFO deposits is:

Institute for Fermentation, Osaka, Juso-homachi 2-17-85, Yodogawa-ku, Osaka, Japan.) The microbiological properties of Pseudomonas sp. MY-1 and Fusarium sp. MY-2 are described in detail in Japanese Patent Kokai 64-10996. Needless to say, any mutant strain derived from the above mentioned microorganisms by an artificial means for mutation can be used in the inventive method provided that the strain has an activity to convert the racemic 2-substituted nitrile compound into the optically active 2-substituted carboxylic acid. It should also be noted that the microorganism used in the inventive method is not limited to those capable of directly converting the nitrile compound into the carboxylic acid, but includes those capable of finally producing the 2-substituted carboxylic acid through an intermediate compound such as a carboxylic acid amide represented by the general formula

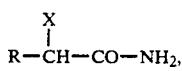

in which R and X each have the meaning defined before, or any other compounds. The above mentioned carboxylic acid amide can be in the form of a racemic compound or an optically active compound.

The microorganism can be used in the inventive method in any desired form including the microbial cells at the proliferation stage, microbial cells at the resting stage such as those contained in the culture medium after completion of culturing of the microorganism, immobilized microbial cells, crushed microbial cells and the like as well as the extracted materials from the microbial cells. The immobilization of the microbial cells can be performed by utilizing a known immobilization technique such as the carrier-bonding method, crosslinking method, inclusion method and the like. The effective extracted material can be obtained by an extracting method in which the microbial cells in a suspension are subjected to crushing by utilizing ultrasonic waves, French press, highpressure homogenizer and the like followed by solid-liquid separation by, for example, centrifugation to give the soluble fraction.

The medium for culturing the above described microorganism is not particularly limitative provided that the medium contains a carbon source, nitrogen source and other necessary nutritive ingredients and is capable of promoting growth of the microorganism having an activity to convert a racemic 2-substituted nitrile compound represented by the general formula (II) into the optically active 2-substituted carboxylic acid represented by the general formula (I). The compound to serve as the carbon source is exemplified by glucose, ethyl alcohol, glycerin, acetone and the like. In addition to the nitrogen source material used in conventional culture media of microorganisms such as inorganic nitrates, ammonium salts, yeast extract, corn steep liquor and the like, it is preferable that the culture medium is admixed with an inducing substance of a nitrile hydrolysis enzyme such as acetonitrile, acetamide, methacrylamide and the like or with at least one kind selected from acetonitrile, methacrylonitrile, methacrylamide, propionitrile and propionamide. It is preferable that the culture medium is admixed with an iron salt in a concentration in the range from 1 to 500 mg/liter. It is of course optional that the culture medium is admixed with various kinds of inorganic salts such as magnesium salts, calcium salts, phosphates and the like as well as other nutritive ingredients required for the growth of the microorganism.

In another embodiment of the inventive method, the racemic 2-substituted nitrile compound is brought into contact with a first enzyme capable of converting the nitrile compound into the carboxylic acid amide represented by the above given general formula (III) and a second enzyme capable of converting the carboxylic acid amide into the desired optically active 2-substituted carboxylic acid of the general formula (I) or brought into contact with an enzyme capable of converting the racemic 2-substituted nitrile compound into the desired optically active 2-substituted carboxylic acid. Various enzymes of microbiological origin are available including endoenzymes and exoenzymes, and can be used in the inventive method without particular limitations. In particular, usable enzymes include those produced by the above mentioned microorganisms.

The 2-substituted nitrile compound of the general formula (II) can be brought into contact with these microorganism or enzyme in any desired manner without particular limitations. For example, the nitrile compound is added to a medium containing the microorganism or enzyme at one time or portion-wise in several times. It is preferable, however, that the nitrile compound is added to the medium continuously but slowly or in several small portions in order that the concentration of the nitrile compound is kept not excessively high in the medium. The amount of the racemic 2-substituted nitrile compound added to the medium is preferably in the range from 1 to 300 g per liter of the medium. When the nitrile compound is brought into contact with the microorganism, the nitrile compound is added to the culture medium of the microorganism at any moment either before inoculation of the medium with the microorganism or during or after culture of the microorganism. It is of course optional that the nitrile compound is added to a suspension of the microbial cells collected from the cultured broth.

When the process of the inventive method proceeds in two steps through an intermediate such as the carboxylic acid amide and the like, the microorganism or enzyme for converting the intermediate into the final product need not be added to the medium at the start of the process but may be added at an appropriate later stage.

The conditions of the biochemical reaction of the racemic 2-substituted nitrile compound of the general formula (II) in contact with the microorganism or enzyme should be controlled depending on the kind of the microorganism or enzyme. When the reaction is performed in the presence of the microorganism, the medium having a pH in the range from 4 to 11 or, preferably, from 6 to 9 is kept at a temperature in the range from 0° to 60° C. or, preferably, from 3° to 30° C. About the same conditions as above are applicable when an enzyme is used in place of the microorganism.

After completion of the reaction, the optically active 2-substituted carboxylic acid produced in the medium is isolated from the medium and purified in a conventional manner by one or a combination of the methods used for the purification of organic compounds such as the method of adsorption on active carbon, method using an ion exchange resin, extraction method, distillation method and the like.

Examples of the optically active 2-substituted carboxylic acid which can be prepared by applying the inventive method include 2-methylbutyric acid of the formula $CH_3=CH_2CH(CH_3)COOH$, 2-methyl-3-butenic acid of the formula $CH_2=CH-CH(CH_3)COOH$, 2-methylpentanoic acid of the formula $CH_3(CH_2)_2CH(CH_3)COOH$, 2-methylhexanoic acid of the formula $CH_3(CH_2)_3CH(CH_3)COOH$, 3-hydroxy-2-methylpropionic acid of the formula $HOCH_2CH(CH_3)COOH$, 3-sulfuhydroxy-2-methylpropionic acid of the formula $HSCH_2CH(CH_3)COOH$, 3-amino-2-methylpropionic acid of the formula $NH_2CH_2CH(CH_3)COOH$, 2-chloropropionic acid of the formula $CH_3CHClCOOH$, 2-methyl-3-chloropropionic acid of the formula $ClCH_2CH(CH_3)COOH$, 2,3-dichloropropionic acid of the formula $ClCH_2CHClCOOH$, 2-chlorobutyric acid of the formula $CH_3CH_2CHClCOOH$, 2,3-dichlorobutyric acid of the formula $CH_3CHClCHClCOOH$, 2-phenylpropionic acid of the formula $CH_3CH(C_6H_5)COOH$, 2-(4-isobutylphenyl)propionic acid of the formula $CH_3CH[C_6H_4-CH_2CH(CH_3)_2]COOH$, in which $C_6H_4$ is a 1,4-phenylene group, 2-(6-methoxy-β-naphthylpropionic acid of the formula $CH_3CH[C_{10}H_6-OCH_3]COOH$, in which $C_{10}H_6-OCH_3$ is a 6-methoxy-β-naphthyl group, 2,2-dimethylcyclopropanecarboxylic acid of the formula

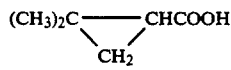

and the like.

In the embodiment of the present invention for the preparation of an optically active 2-substituted carboxylic acid, it is possible to concurrently produce an optically active 2-substituted carboxylic acid amide or an optically active 2-substituted nitrile compound corresponding to the 2-substituted carboxylic acid which is the antipode of the optically active 2-substituted carboxylic acid as the desired product. Therefore, the optically active antipode carboxylic acid can be obtained by isolating the 2-substituted carboxylic acid amide or nitrile compound from the reaction mixture by a conventional procedure followed by hydrolysis of the amide or nitrile compound.

In the following, the method of the present invention is described in more detail by way of examples.

EXAMPLE 1

A strain of Pseudomonas sp. MY-1 (FERM P-9174, FERM BP-2541) was inoculated to 1500 ml of a culture medium containing 10 g/liter of glycerin, 5 g/liter of acetonitrile, 0.5 g/liter of potassium dihydrogen phosphate $KH_2PO_4$, 5 g/liter of disodium hydrogen phosphate dodecahydrate $Na_2HPO_4.12H_2O$, 0.2 g/liter of magnesium sulfate heptahydrate $MgSO_4.7H_2O$, 0.01 g/liter of calcium chloride dihydrate $CaCl_2.2H_2O$, 0.01 g/liter of iron (II) sulfate $FeSO_4$, 0.05 g/liter of yeast extract and 0.05 g/liter of corn steep liquor and cultured therein at 30° C. for 24 hours.

After cultivation, the microbial cells were separated from the culture medium and washed and then suspended in 30 ml of deionized water. The suspension having a pH controlled at 7.5 to 7.8 was kept at a temperature of 15° C. and a 180 mg portion of 2-chloropropionitrile was added thereto in every 5 minutes over a period of 150 minutes under agitation. After 90 minutes of further continued agitation to complete the reaction, the suspension was subjected to centrifugal separation to remove the microbial cells. The reaction mixture freed from the microbial cells was fractionated by a conventional method using ether to give 1.3 g of an acidic fraction and 4.5 g of a neutral fraction. The acidic fraction was purified by using ether and a 5% aqueous solution of sodium carbonate until a single peak was obtained in the gas chromatogram for 2-chloropropionic acid. The thus obtained 2-chloropropionic acid had a specific rotation of $[\alpha]_D = -6.7$ in ethyl alcohol. The neutral fraction was subjected to a gas chromatographic analysis using a Thermon 3000 column packed with Celite 545 to find that the purity of 2-chloropropionamide therein was 93%. The specific rotation of the fraction was $[\alpha]_D = +13.0$ in ethyl alcohol.

EXAMPLE 2

The experimental procedure was substantially the same as in Example 1 described above except that 2-chloropropionitrile was replaced with 3-chloro-2-methylpropionitrile which was added in 180 mg portions in every 5 minutes over a period of 100 minutes. As a result, 1.15 g of an acidic fraction and 1.3 g of a neutral fraction were obtained. The acidic fraction was subjected to a gas chromatographic analysis to find that the gas chromatogram had a single peak corresponding to 3-chloro-2-methyl propionic acid. The specific rotation thereof was $[\alpha]_D = +1.8$ in ethyl alcohol. The neutral fraction was purified by recrystallization using ethyl acetate and n-hexane. The thus obtained 3-chloro-2-methylpropionamide had a specific rotation of $[\alpha]_D = -5.8$ in ethyl alcohol.

EXAMPLE 3

The experimental procedure was substantially the same as in Example 1 except that the 2-chloropropionitrile was replaced with 2-methylbutyronitrile which was added in 180 mg portions in every 5 minutes over a period of 60 minutes. As a result, 1.4 g of an acidic fraction and 0.7 g of a neutral fraction were obtained. The acidic fraction was subjected to a gas chromatographic analysis to find that the gas chromatogram had a single peak of 2-methylbutyric acid. The specific rotation thereof was $[\alpha]_D = +8.5$ in ethyl alcohol. The neutral fraction was crystallized by using ethyl acetate and n-hexane. The thus obtained 2-methyl butyroamide had a specific rotation of $[\alpha]_D = +23.8$ in ethyl alcohol.

EXAMPLE 4

The experimental procedure was substantially the same as in Example 1 except that the 2-chloropropionitrile in Example 1 was replaced with 2-methyl-3-butenonitrile which was added in 180 mg portions in every 5 minutes over a period of 60 minutes to give 1.2 g of an acidic fraction and 1.4 g of a neutral fraction. The acidic fraction was subjected to a gas chromatographic analysis to find that the gas chromatogram had a single peak of 2-methyl-3-butenoic acid. The specific rotation thereof was $[\alpha]_D = +18.0$ in ethyl alcohol. The neutral fraction was crystallized by using ethyl acetate and n-hexane. The thus obtained 2-methyl-3-butenamide had a specific rotation of $[\alpha]_D = = 6.3$ in ethyl alcohol.

EXAMPLE 5

A strain of Fusarium sp. MY-2 (FERM P-9187, FERM BP-2542) was inoculated to 100 ml of a culture medium containing 10 g/liter of glycerin, 5 g/liter of acetonitrile, 0.5 g/liter of potassium dihydrogen phosphate $KH_2PO_4$, 5 g/liter of disodium hydrogen phosphate dodecahydrate $Na_2HPO_4.12H_2O$, 0.2 g/liter-of magnesium sulfate heptahydrate $MgSO_4.7H_2O$, 0.01 g/liter of calcium chloride dihydrate $CaCl_2.2H_2O$, 0.01 of yeast extract and 0.05 g/liter of corn steep liquor and cultured therein at 30° C. for 28 hours. After cultivation, the microbial cells collected from the culture medium were washed and suspended in 10 ml of a 1/15 M phosphate buffer solution (pH 8). 100 µl of 2-methylbutyronitrile was add to the suspension, and the resultant suspension was kept at 15° C. for 5 hours to effect the reaction followed by adjustment of the pH to 2 with addition of a 6N hydrochloric acid and then freed from the microbial cells by centrifugation. The reaction mixture freed from the microbial cells was subjected to a gas chromatographic analysis using a Thermon 3000 column packed with Celite 545 to quantitatively determine 2-methylbutyric acid. The result was that the amount of the acid produced was 2 g/liter. 2-Methylbutyramide could hardly be detected by the gas chromatography. The thus obtained 2-methylbutyric acid was subjected to extraction with ether and converted into an amide of (S)-1-(1-naphthyl)ethyl amine followed by a high-performance liquid chromatography on a Unisil Q100-5 column using a 4:1 mixture of n-hexane and tetrahydrofuran as the solvent for the determination of the optical purity to give a result that the purity of the (S)-2-methyl butyric acid was 71%ee.

EXAMPLE 6

The experimental procedure was substantially the same as in Example 5 except that the 2-methyl butyronitrile in Example 5 was replaced with 2-methyl-3-butenonitrile. As a result, it was found that 2-methyl-3-butenoic acid having an optical purity of 30%ee was produced in a yield of 3.5 g/liter. 2-Methyl-3-butenamide was hardly detected in the reaction mixture.

EXAMPLE 7

The experimental procedure was substantially the same as in Example 5 except that the 2-methylbutyronitrile in Example 5 was replaced with 2-methyl-3-chloropropionitrile and the reaction was performed for 3 hours instead of 5 hours. The result was that 2-methyl-3-chloropropionic acid having an optical purity of 40%ee was obtained in a yield of 4.8 g/liter.

COMPARATIVE EXAMPLE 1

The experimental procedure was substantially the same as in Example 5 except that the reaction was undertaken by adding 1 g/liter of 2-methyl butyramide in place of 2-methylbutyronitrile. The result was that 2-methylbutyric acid could not be detected in the reaction mixture without decrease in the content of the starting 2-methylbutyramide.

EXAMPLE 8

A strain of Pseudomonas sp. MY-1 (FERM P-9174, FERM BP-2541 ) was inoculated to 400 ml of a culture medium containing 10 g/liter of glycerin, 5 g/liter of methacrylamide, 0.5 g/liter of potassium dihydrogen phosphate $KH_2PO_4$, 5 g/liter of sodium hydrogen phosphate dodecahydrate $Na_2HPO_4.12H_2O$, 0.2 g/liter of magnesium heptahydrate $MgSO_4.7H_2O$, 0.01 g/liter of calcium chloride dihydrate $CaCl_2.2H_2O$, 0.01 g/liter of iron sulfate heptahydrate $FeSO_4.7H_2O$, 0.05 g/liter of yeast extract and 0.05 g/liter of corn steep liquor and cultured therein at 30° C. for 18 hours. After cultivation, the microbial cells were collected from the culture medium followed by washing and then the microbial cells were suspended in 20 ml of a 1/15M phosphate buffer solution (pH 8). In the next place, 200 mg of 1-cyano-2,2-dimethylcyclopropane were added to the suspension of the microbial cells to effect the reaction at 15° C. for 65 hours followed by centrifugal separation to remove the microbial cells from the mixture. The reaction mixture freed from the microbial cells was subjected to separation in a conventional manner by using ether to give 130 mg of an acidic fraction and 89 mg of an amide fraction The specific rotation of the 2,2-dimethylcyclopropanecarboxylic acid obtained from the acidic fraction was $[\alpha]_D = +108$ in ethyl alcohol while that of the 2,2-dimethylcyclopropanecarboxylic acid amide obtained from the amide fraction was $[\alpha]_D = -81$ in ethyl alcohol. The above given specific rotation of the 2,2-dimethylcyclopropanecarboxylic acid indicated that it was the S-isomer. Further, the 2,2-dimethylcyclopropanecarboxylic acid was converted to an amide with (S)-1-(1-naphthyl) ethylamine and the amide compound was subjected to the high-performance liquid chromatography on a Unisil Q100-5 column with a 4:1 mixture of n-hexane and tetrahydrofuran as the solvent to find that the optical purity thereof was 84%ee.

EXAMPLE 9

The experimental procedure was substantially the same as in Example 8 for the culturing of the microorganism and the microbiological reaction except that the reaction time with the microorganism was 5 hours instead of 65 hours. The reaction mixture freed from the microbial cells was subjected to the gas chromatographic analysis using a Thermon 3000 column packed with Celite 545 at a column temperature of 120° C. to find that the contents of 2,2-dimethylcyclopropanecarboxylic acid and 2,2-dimethylcyclopropanecarboxylic acid amide were 45 mg/20 ml and 180 mg/20 ml, respectively. The thus obtained 2,2-dimethylcyclopropanecarboxylic acid was the S-isomer having an optical purity of 100% ee.

EXAMPLE 10

A strain of Pseudomonas sp. MY-1 (FERM P-9174, FERM BP-2541) was inoculated to 100 ml of the same culture medium as used in Example 8 and cultured therein at 30° C. for 18 hours. After cultivation, the microbial cells collected from the culture medium and washed were suspended in 10 ml of a 1/15M phosphate buffer solution (pH 8). In the next place, the suspension was admixed with 100 mg of 2-methyl-3-butenonitrile and the reaction was performed at 15° C. for 15 minutes followed by centrifugal separation of the suspension to remove the microbial cells. The reaction mixture freed from the microbial cells was subjected to the gas chromatographic analysis under the same conditions as in Example 9 to find that the contents of 2-methyl-3-butenoic acid and 2-methyl-3-butenamide were 43 mg/10 ml and 72 mg/10 ml, respectively. The thus obtained 2-methyl-3-butenoic acid had an optical purity of 40%ee.

EXAMPLES 11 to 15

The experimental procedure in each of these examples was substantially the same as in Example 10 except that the Pseudomonas sp. MY-1 (FERM P-9174, FERM BP-2541) was replaced with the microorganism indicated in Table 1 below, the 2-methyl-3-butenonitrile was replaced with 2-chloropropionitrile and the reaction time was 60 minutes instead of 15 minutes. The reaction mixture was subjected to the gas chromatographic analysis using a Thermon 3000 column packed with Celite 545 at a column temperature of 140° C. for the quantitative determination of 2-chloropropionic acid and 2-chloroprppionamide to give the results shown in Table 1 which also shows the result of the measurement for the optical purity of the 2-chloropropionic acid in each of the examples.

TABLE 1

| Example No. | Strain of microorganism | Amount produced, mg/10 ml | | Optical purity % ee |
|---|---|---|---|---|
| | | 2-chloro-propionic acid | 2-chloro-propion-amide | |
| 11 | Rhodococcus erythroporys IFO 12320 | 39 | 85 | 35 |
| 12 | Brevibacterium imperial B222 CBS 498.74 | 1 | 6 | 28 |
| 13 | Micrococcus sp. A111 CBS 497.74 | 2 | 28 | 30 |
| 14 | Bacteridium sp. R341 CBS 496.74 | 6 | 69 | 48 |
| 15 | Bacillus sp. CBS 494.74 | 2 | 7 | 24 |

EXAMPLE 16

The experimental procedure was substantially the same as in Example 10 except that the 2-methyl-3-butenonitrile was replaced with 2-methylhexylonitrile. The reaction mixture freed from the microbial cells was subjected to the gas chromatographic analysis using a Thermon 3000 column packed with Celite 545 for the quantitative determination of 2-methylhexanoic acid and 2-methylhexanamide to find that the contents thereof were 12 mg/10 ml and 63 mg/10 ml, respectively. The 2-methyl hexanoic acid had an optical purity of 78% ee.

What is claimed is:

1. A microbiological method for the preparation of an optically active carboxylic acid of the formula

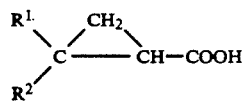

in which $R^1$ and $R^2$ are independently a lower alkyl group, which method comprises (a) contacting a racemic nitrile of the formula

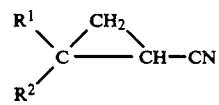

with a microorganism capable of converting the racemic nitrile into the optically active carboxylic acid, and wherein the microorganism is selected from the group consisting of Pseudomonas sp. MY-1, FERM BP-2541, and Fusarium sp. MY-2, FERM BP-2542; and (b) recovering said optically active carboxylic acid.

2. The microbiological method as claimed in claim 1, wherein $R^1$ and $R^2$ are both methyl groups.

3. The microbiological method as claimed in claim 1 wherein the racemic nitrile is brought into contact with the microorganism in an aqueous medium in which the microbial cells of the microorganism are suspended.

4. The microbiological method as claimed in claim 3 wherein the concentration of the racemic nitrile in the aqueous medium is in the range from 1 to 300 g per liter.

5. The microbiological method as claimed in claim 1 wherein the aqueous medium has a pH in the range from 6 to 9.

6. The microbiological method as claimed in claim 3 wherein the racemic nitrile is brought into contact with the microorganism in the aqueous medium at a temperature in the range from 3° to 30° C.

7. The microbiological method of claim 1 wherein said microorganism is Pseudomonas sp. MY-1 FERM BP-2541.

8. The microbiological method of claim 1, wherein said microorganism is Fusarium sp. MY-2 FERM BP-2542.

* * * * *